Dec. 24, 1963 L. MORO Plant Pat. 2,333
ROSE PLANT
Filed Jan. 10, 1963
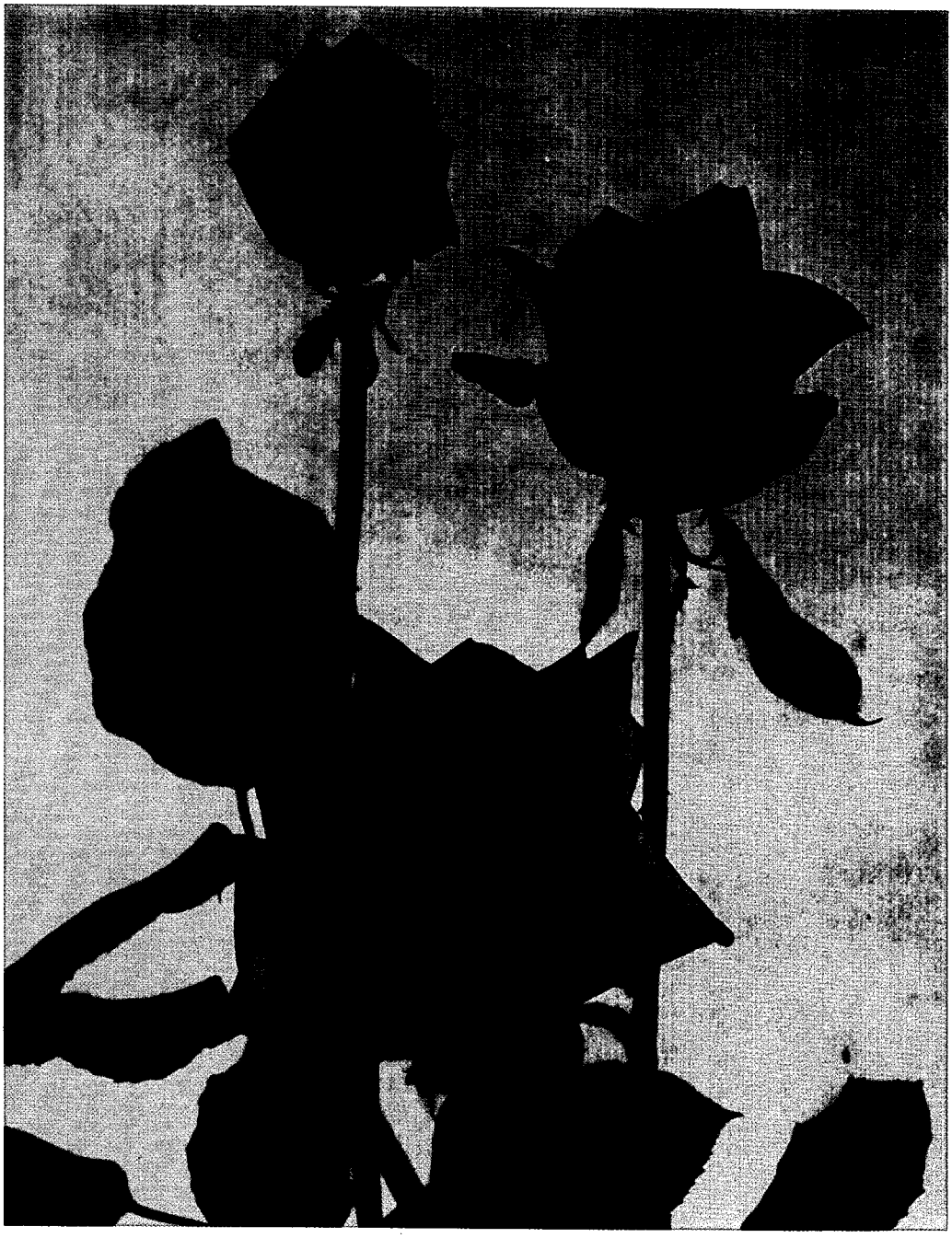
Inventor.
Luciano Moro
By: Robb & Robb
Attorneys.

United States Patent Office

Plant Pat. 2,333
Patented Dec. 24, 1963

2,333
ROSE PLANT

Luciano Moro, San Remo, Italy, assignor to Carlton Rose Nurseries, Carlton, Oreg., a corporation of Oregon Filed Jan. 10, 1963, Ser. No. 250,725
1 Claim. (Cl. Plt.—21)

The present invention relates to a new and distinct variety of rose plant of the hybrid tea class, which was originated by me by crossing the variety known as "Volcano" (U.S. Plant Patent No. 951) with the variety "Rouge Meilland," known in the United States as "Happiness" (U.S. Plant Patent No. 911).

The primary objective of this breeding was to produce an improved rose variety, and more particularly superior to the rose variety "Happiness" which is probably the top premium red rose that is grown under glass in the United States at the present time for the commercial production of cut flowers, but the flowers of which have a tendency to turn dark in color during the short, dark days of winter, as well as a tendency to reduce its flower productivity during the winter season as the result of "blind" wood which does not bloom at that time of year under glass. My new variety fully overcomes these problems, and, accordingly, the aforementioned objectives have been achieved, along with other desirable improvements, as evidenced by the following unique combination of characteristics which are outstanding in the new variety and which distinguish it from its parents, as well as from all other varieties of which I am aware:

(1) A vigorous habit of growth which is maintained during the winter season and which is superior to the vigor of both parent varieties;

(2) A prolific and relatively rapid production of commerically salable flowers of excellent quality and which constitutes an important asset to the commercial grower during the winter season when the cut flower market is best and more profitable;

(3) A distinctive, attractive and brilliant red color of the flowers, said color being slightly lighter at all times than the color of the flowers of either parent variety which tend to darken considerably during the short, dark days of winter when grown under glass;

(4) A uniform color of the flower petals and prolonged retention of the flower color both on the bush and when cut for cut flower production; and (5) Good flower petalage which is considerably greater than the petalage of the flowers of either parent variety.

In comparison with the parent varieties, my new variety has a desirable feature resulting from a slightly lighter flower color than the flower color of either parent variety, and the color of the new variety is retained throughout the year; the flowers have many more petals and the plants will produce more salable flowers in a shorter period of time than either of the parent varieties, which is a very important factor in the highly competitive field of commercial cut flower production; and the flowers of the new variety are "loose" enough so that they will open to full maturity under adverse conditions, with consequent production of top quality blooms at all times, and retention of full productive vigor attributable to far less "blind" wood than is characteristic of either parent variety.

Asexual reproduction of my new variety by budding in San Remo, Italy, as well as under glass at Hillsboro, Oregon, U.S.A., and in the fields at Carlton and Gaston, Oregon, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart issued by the British Colour Council in collaboration with The Royal Horticultural Society, except where general color terms of ordinary dictionary significance are obvious:

Type: Hardy; tall; bush; greenhouse and outdoor; seedling; for cut flowers and for garden decoration.
Class: Hybrid tea.
Breeding: Seedling.
*Seed parent.*—"Volcano."
*Pollen parent.*—"Happiness."
Propagation: Holds its distinguishing characteristics through succeeding propagations by budding.

*Flower*

Locality where grown and observed: Gaston, Oregon, and Carlton, Oregon, U.S.A.
Continuity: Continuous.
Fragrance: Moderate.
Flowers borne: Singly; regular; on strong, long stems.
Quantity of bloom: Abundant, both outdoors and in greenhouse.
Bud:
*Peduncle.*—Medium length; heavy; erect; somewhat rough; with few yellow prickles. Color—dark green.
*Before calyx breaks.*—Size—large. Form—pointed tip; oval base; with a conspicuous neck; with foliaceous appendages on the surface of the bud; with slender, much-cut foliaceous parts extending beyond the tip of the bud equal to ½ of its length. Color—Scheele's Green, Plate 860.
*As calyx breaks.*—Color—Ruby Red, Plate 827/1.
*As first petal opens.*—Size—large. Form—long; ovoid. Color: outside—Chrysanthemum Crimson, Plate 824/2; inside—Indian Lake, Plate 826/2.
*Opening.*—Opens up well; is retarded in opening by cold weather.
Bloom:
*Size (when fully open).*—Large; from 4½ inches to 5½ inches.
*Petalage.*—Very double (usually with stamens showing); from 46 to 50 petals; arranged regularly.
*Form.*—Flat, but high-centered at first, and becoming very flat-centered; petals at first being loosely cupped and rolled inward, but later becoming loosely cupped and rolled outward at maturity.
Petals:
*Texture.*—Thick; leathery.
*Appearance.*—Inside—velvety. Outside—satiny.
*Shape.*—Outside—round, with one notch. Intermediate—round, with one notch. Inside—oval, with one notch.

As observed in both the newly opened and three-days open flowers grown in a greenhouse at Carlton, Oregon, U.S.A., the color of the flower petals is uniform throughout each flower, with the color of the outside surface of each petal being Chrysanthemum Crimson, Pate 824/2, and with the color of the inside petal surface being Indian Lake, Plate 826/2, and these colors are maintained for an extended period.

*General color effect.*—Newly open flower—crimson red. Three-days open—crimson red.
*Behavior.*—Persists; fading brown; retarded by cold, but literally immune to summer heat.
*Flower longevity.*—On bush in garden—from 5 to 7 days in September. Cut roses grown outdoors and kept at living-room temperatures—6 days in September. Cut roses grown in greenhouse and kept at living-room temperatures—6 days in September.

*Reproductive Organs*

Stamens: Many; arranged regularly about pistils.
Filaments: Medium length; many with anthers. Color—Cherry, Plate 722/1.
Anthers: Large; all open at once. Color—Yellow Ochre, Plate 07/1.
Pollen: Abundant. Color—golden yellow.
Pistils: Many.
Styles: Uneven; medium length; medium heavy; bunched and columnar.
Stigma: Color—light yellow.
Ovaries: All enclosed in calyx.
Hips: Globular; with conspicuous neck; smooth; thick walls. Color—scarlet.
Sepals: Permanent; moderately long; spear-shaped; curled. Color—Scheele's Green, Plate 860/1.
Seeds: Many; large.

*Plant*

Foliage:

*Leaves.*—Compound of 5–7 leaflets; normal abundance; medium large; heavy; leathery.

*Leaflet.*—Shape—ovate, with apex acute. Base—acute. Margin—simply serrate.

*Color.*—Mature: upper surface—dark green; under surface—normal light green. Young: upper surface—bright red; under surface—light bronze red.

*Rachis (the supporting stem of the compound leaf).*—Heavy. Upper side—smooth. Under side—moderately prickly.

*Stipules.*—Moderately long; moderately wide; with medium long points turning out at an angle more than 45°.

*Disease resistance.*—Excellent resistance to mildew and blackspot, and does very well under general climatic conditions, with especially good heat resistance in summer, as determined by comparison with other varieties grown under comparable cultural conditions at Carlton, Oregon, U.S.A.

Growth:

*Habit.*—Upright; much-branched.

*Growth.*—Free and vigorous.

*Canes.*—Heavy.

*Main stems.*—Color—bright green. Thorns—many; medium length; hooked downward; with long, narrow base. Prickles—none. Hairs—none.

*Branches.*—Color—bright green. Thorns—many; medium length; hooked downward; with long, narrow base. Prickles—none. Hairs—none.

*New shoots.*—Color—bright bronze red. Thorns—many; medium length; hooked downward; with long, narrow base. Prickles—none. Hairs—none.

I claim:

A new and distinct variety of rose plant of the hybrid tea class, substantially as herein shown and described, characterized particularly as to novelty by the unique combination of a vigorous habit of growth, prolific and relatively rapid production of commerically salable flowers of excellent quality, a distinctive, attractive and brilliant red color of the flowers which is slightly lighter at all times than the color of the flowers of either parent variety, uniformity of the color of the flower petals throughout each flower and prolonged retention of the flower color both on the bush and when cut, said flower color persisting during the relatively short and dark days of winter seasons when grown under glass, and a much greater flower petalage than the flowers of either parent variety.

No references cited,